(12) United States Patent
Huang

(10) Patent No.: US 9,833,582 B2
(45) Date of Patent: Dec. 5, 2017

(54) NEBULIZER AND NOZZLE THEREOF

(71) Applicant: Yi-Hsin Huang, New Taipei (TW)

(72) Inventor: Yi-Hsin Huang, New Taipei (TW)

(73) Assignee: TAIDOC TECHNOLOGY CORPORATION, New Taipei (TW)

( * ) Notice: Subject to any disclaimer, the term of this patent is extended or adjusted under 35 U.S.C. 154(b) by 895 days.

(21) Appl. No.: 13/623,963

(22) Filed: Sep. 21, 2012

(65) Prior Publication Data

US 2013/0081624 A1 Apr. 4, 2013

(30) Foreign Application Priority Data

Oct. 3, 2011 (TW) .............................. 100135813 A
Aug. 31, 2012 (TW) .............................. 101131799 A

(51) Int. Cl.
| | | |
|---|---|---|
| A61M 11/02 | (2006.01) | |
| A61M 11/00 | (2006.01) | |
| A61M 15/00 | (2006.01) | |
| A61M 11/06 | (2006.01) | |
| B05B 1/26 | (2006.01) | |
| B05B 7/00 | (2006.01) | |
| B05B 7/24 | (2006.01) | |

(52) U.S. Cl.
CPC ......... *A61M 11/002* (2014.02); *A61M 11/003* (2014.02); *A61M 11/06* (2013.01); *A61M 15/0021* (2014.02); *B05B 1/262* (2013.01); *B05B 7/0012* (2013.01); *B05B 7/2424* (2013.01)

(58) Field of Classification Search
CPC .. A61M 11/002; A61M 11/06; A61M 11/003; A61M 11/08; A61M 15/0021
See application file for complete search history.

(56) References Cited

U.S. PATENT DOCUMENTS

| | | | | |
|---|---|---|---|---|
| 5,054,477 A | * | 10/1991 | Terada ................... | A61M 11/06 128/200.14 |
| 5,209,225 A | * | 5/1993 | Glenn .................... | A61M 11/06 128/200.14 |
| 5,241,954 A | * | 9/1993 | Glenn .................... | A61M 11/06 128/200.18 |
| 5,505,193 A | * | 4/1996 | Ballini .................. | A61H 35/04 128/200.14 |
| 6,129,080 A | * | 10/2000 | Pitcher .................. | A61M 11/06 128/200.14 |
| 6,363,932 B1 | * | 4/2002 | Forchione ......... | A61M 15/0086 128/200.14 |

(Continued)

*Primary Examiner* — Justine Yu
*Assistant Examiner* — Timothy Stanis
(74) *Attorney, Agent, or Firm* — Chun-Ming Shih

(57) ABSTRACT

A nebulizer and a nozzle thereof are provided. The nozzle has a containing seat and a cover. The containing seat has an air conduit. The air conduit has an input terminal and an output terminal. The cover has a guiding channel and an impediment. An input opening is formed in the nozzle for introducing air. A first opening of the guiding channel is disposed near the output terminal and the input opening is disposed far of the output terminal. The impediment is disposed in front of the output terminal and has a plane. Air emitted from the output terminal lashes the plane and then flows to a second opening of the guiding channel, and the air of the input opening is guided to the first opening for decreasing a whole resistance of the nozzle, and thereby increasing nebulization efficiency.

20 Claims, 10 Drawing Sheets

(56) References Cited

U.S. PATENT DOCUMENTS

| | | | |
|---|---|---|---|
| 7,841,335 B2* | 11/2010 | Harrington | A61M 11/06 128/200.14 |
| 2003/0136399 A1* | 7/2003 | Foley | A61M 11/06 128/200.14 |
| 2003/0197068 A1* | 10/2003 | Abate | A61M 11/06 239/338 |
| 2004/0031485 A1* | 2/2004 | Rustad | A61M 11/00 128/200.18 |
| 2005/0145243 A1* | 7/2005 | Trombi | A61M 11/002 128/200.14 |
| 2007/0068513 A1* | 3/2007 | Kreutzmann | A61M 11/06 128/200.14 |
| 2007/0175469 A1* | 8/2007 | Rohrschneider | A61M 15/0065 128/200.23 |
| 2007/0227536 A1* | 10/2007 | Rivera | A61M 11/06 128/200.21 |
| 2009/0281482 A1* | 11/2009 | Baker | A61M 1/0058 604/28 |
| 2010/0001098 A1* | 1/2010 | So | B05B 1/046 239/266 |
| 2010/0319687 A1* | 12/2010 | Esaki | A61M 11/06 128/200.23 |
| 2011/0114090 A1* | 5/2011 | Piper | A61M 11/06 128/200.23 |
| 2011/0247610 A1* | 10/2011 | Nakamura | A61M 11/02 128/200.14 |

* cited by examiner

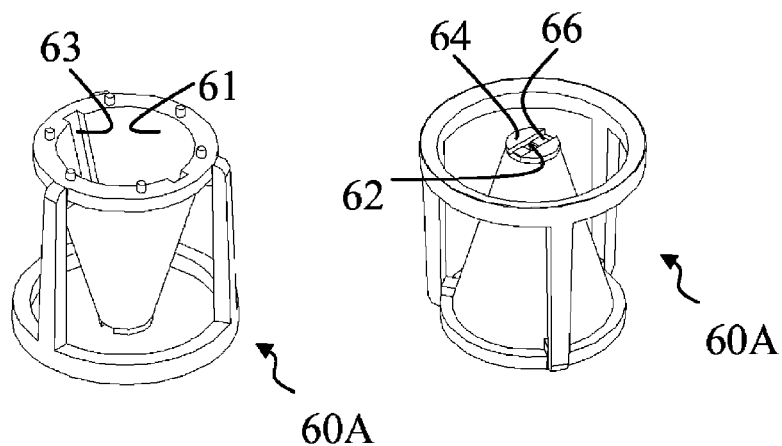
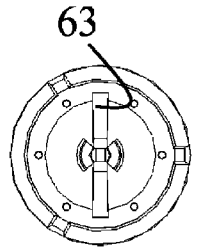 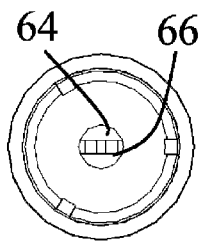 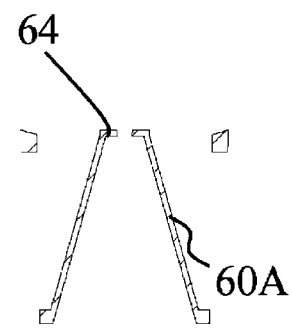
FIG. 10B    FIG. 10A
FIG. 10C    FIG. 10D    FIG. 10E

NEBULIZER AND NOZZLE THEREOF

BACKGROUND OF THE INVENTION

Field of the Invention

The present invention relates in general to a nebulizer, and particularly relates to a nozzle of the nebulizer.

Description of the Related Art

A nebulization for respiratory tract disease treatment is one of popularity medical therapy for recent years. The nebulized particle can inhale from the nose and mouth into the bronchiole then diffuse to whole alveoli so that nebulized drug is absorbed completely in the human body for well treatment. Generally speaking, the way of nebulization has pneumatic and ultrasonic types, and the pneumatic nebulization needs a pump and a nozzle.

The nozzle operation will generate a resistance caused by many factors, for example, the structure of nozzle, the specification of a nebulizer and so on. The above descriptive factors also affect the size of nebulized particle. Furthermore, the higher resistance of the nozzle needs more power consumption to drive it so that the desirable nebulized particle size has been achieved more than 35 watts power consumption of the nebulizer on the present market. However, higher power consumption of the pump has a larger size of the pump and enhances the noise interference and more electricity waste so as to inconvenience for users to carry and use.

Thus, there is an important issue for manufacturer to design high efficiency and low resistance of the nozzle.

SUMMARY OF THE INVENTION

According to one aspect of the present invention is to provide a nebulizer for achieving the desirable nebulized particle size by using less power consumption of the pump.

According to another aspect of the present invention is to provide a nozzle for a nebulizer for increasing the nebulization rate.

In one aspect of the present invention, the present invention provides a nozzle for a nebulizer, comprising a containing seat, an input opening, a liquid delivery structure and a cover. The containing seat comprises an air conduit and a liquid container. The air conduit has an input terminal and an output terminal, and the liquid container is used for storing liquid. The input opening is used for introducing air. The liquid delivery structure is assembled in the liquid container and extending from the liquid container toward the output terminal. The cover assembled with the containing seat and having a circumference zone and an inner zone, and the input opening disposed at the circumference zone of the cover, the cover which comprises a guiding channel and an impediment. The guiding channel has a first opening and a second opening, and the first and the second opening both disposed at the inner zone of the cover and oppositely to each other. The first opening is communicated with the input opening, wherein the first opening is near the output terminal and the input opening is away from the output terminal. The impediment is disposed facing to the output terminal wherein air emitted from the output terminal is configured to flow to the second opening of the guiding channel in order to guide the air introduced at the input opening that flowed to the first opening.

In an embodiment in accordance with the present invention, the impediment comprises a small surface facing to the output terminal and the air emitted from the output terminal lashed the small surface. Preferably, the small surface may be a small plane or a curved surface. The width of the small plane is between 0.5 millimeter to 3 millimeter. The nozzle is driven by a pump with the power consumption below 15 watts to produce nebulized particles with a mass median aerodynamic diameter of 5 microns and a diameter of the output terminal is 0.32 millimeter to 0.38 millimeter. The nebulization rate of liquid is between 0.15 cubic centimeters/minute to 0.5 cubic centimeters/minute.

In an embodiment in accordance with the present invention, the input opening may be formed in the containing seat or the cover. The input opening is preferably disposed on periphery from the output terminal, and the first opening is disposed in front of and directly facing the output terminal.

In an embodiment in accordance with the present invention, the cover further comprises a filter disposed in the guiding channel between the impediment and the second opening, and the filter is used to extend a flowing path for the air. The nozzle further comprises an engaging guiding element being used to guide the cover and the containing seat during assembly. The engaging guiding element is preferably a block on an outside of the cover. The nozzle further comprises an engaging recognition element disposed on the cover and the containing seat, and used to recognize an engagement state of the cover and the containing seat. In another aspect in accordance with the present invention, the present invention provides a nebulizer, comprising a nozzle, a pump and an air pipe. The nozzle comprises a containing seat, an input opening, a liquid delivery structure and a cover. The containing seat comprises an air conduit and a liquid container. The air conduit has an input terminal and an output terminal, and the liquid container is used for storing liquid. The input opening is used for introducing air. The liquid delivery structure is assembled in the liquid container and extending from the liquid container toward the output terminal. The cover assembled with the containing seat and having a circumference zone and an inner zone, and the input opening disposed at the circumference zone of the cover, the cover which comprises a guiding channel and an impediment. The guiding channel has a first opening and a second opening, and the first and the second opening both disposed at the inner zone of the cover and oppositely to each other. The first opening is communicated with the input opening, wherein the first opening is near the output terminal and the input opening is away from the output terminal. The impediment is disposed facing to the output terminal and air emitted from the output terminal cause liquid to be lashed against the impediment and subsequently flow through the first opening and the second opening of the guiding channel in order to guide the air introduced at the input opening that flowed to the first opening. The pump is used to pump air into the input terminal. The air pipe is connecting between the pump and the input terminal.

In an embodiment in accordance with the present invention, the impediment comprises a small surface facing to the output terminal and air emitted from the output terminal lashed the small surface. The small surface is a small plane or a curved surface. The width of the small plane is between 0.5 millimeter to 3 millimeter.

In one another aspect in accordance with the present invention, the present invention provides a nozzle for a nebulizer, comprising a containing seat, a liquid delivery structure and a cover. The containing seat comprises an air conduit and a liquid container. The air conduit has an input terminal and an output terminal. The liquid container is used for storing liquid. The liquid delivery structure is assembled in the liquid container and comprising a first delivery opening, a second delivery opening, a first liquid guiding element and a second liquid guiding element. The second delivery opening is disposed oppositely to the first delivery opening to let the liquid transport from the first delivery opening to the second delivery opening. The first liquid guiding element is protruded from the second delivery opening and used to let the liquid spray from the first liquid guiding element. The second liquid guiding element and the first liquid guiding element both are protruding from the second delivery opening, wherein a longitudinal height of the first liquid guiding element is higher than that of the second liquid guiding element. The cover comprises a guiding channel and an impediment. The guiding channel has a first opening and a second opening disposed oppositely to each other. The impediment is disposed in front of and facing to the output terminal, wherein air is configured to be emitted from the output terminal to lashed against the impediment and subsequently flow to the second opening of the guiding channel.

In an embodiment in accordance with the present invention, the liquid delivery structure further comprises a second liquid guiding element protruded from the second delivery opening that does not have the first liquid guiding element protruded. The first liquid guiding element are two semicircle protrusions protruded from and formed oppositely to two sites of the second delivery opening and the second liquid guiding element are two square protrusions protruded respectively and oppositely from the second delivery opening. A longitudinal height of the first liquid guiding element is higher than that of the second liquid guiding element.

According to the aspect of the present invention as description above, the nozzle of the nebulizer comprises an input opening disposed far from the output terminal, a first opening disposed near the output terminal and/or an impediment having a small surface disposed in front of the output terminal so as to increase nebulization efficiency.

In another aspect of the present invention, the nozzle of the nebulizer is disposed a liquid guiding element of the liquid delivery structure for guiding liquid slightly warping then more concentrative emitted from the center so as to achieve well nebulization.

In order to make the symbol and the advantage more realizable in the present invention, the following description and accompanying drawings are some examples in accordance with the present invention.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 10A is a schematic perspective view of the third embodiment of a liquid delivery structure in accordance with the present invention;

FIG. 10B is a schematic perspective view of upside down of the liquid delivery structure in FIG. 10A;

FIG. 10C is a rear perspective view of liquid delivery structure in FIG. 10A;

FIG. 10D is a top perspective view of the liquid delivery structure in FIG. 10A;

FIG. 10E is a cross-sectional view of the liquid delivery structure in FIG. 10A.

DESCRIPTION OF THE PREFERRED EMBODIMENTS

Figure 1:
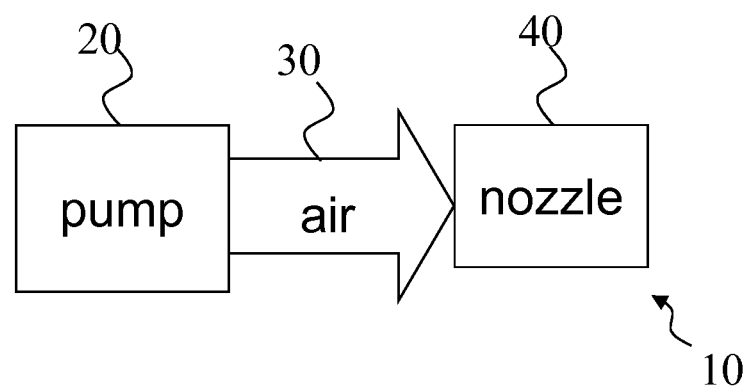
FIG. 1 is a block diagram of a first embodiment of a nebulizer in accordance with the present invention.

For the purposes of promoting an understanding of the principles of the invention, reference will now be made to the embodiment illustrated in the drawings, and specific language will be used to describe that embodiment. It will nevertheless be understood that no limitation of the scope of the invention is intended. Alterations and modifications in the illustrated device, and further applications of the principles of the invention as illustrated therein, as would normally occur to one skilled in the art to which the invention relates are contemplated, are desired to be protected. Such alternative embodiments require certain adaptations to the embodiments discussed herein that would be obvious to those skilled in the art.

A nebulizer and a nozzle thereof of an embodiment in accordance with the present invention are provided. Generally speaking, if the resistance concentrated in some parts of the nozzle, the whole construction resistance of the nebulizer will increase. An embodiment of a nozzle in accordance with the present invention balances each part resistance so that used the pump with a lower power consumption can drive the nozzle for nebulization. In an embodiment in accordance with the present invention, an input opening is disposed on the nozzle. When the air pumped by the pump emitted to an output terminal, the air entered from the input opening is guided to the output terminal so as to decrease the resistance of the nozzle. Furthermore, an impediment of the nozzle having a small plane or a curved surface is disposed in front of the output terminal, and the small plane or the curved surface is facing the output terminal to guide the airflow toward a guiding channel disposed around the impediment so as to decrease the resistance. In addition, the distance set between the output terminal and the impediment influences the air flowing so as to decrease the whole resistance of nozzle. The following description and accompanying drawings are some examples in accordance with the present invention. The same symbol herein in the drawings indicates the same or similar structure.

With reference to FIG. 1, it is a block diagram of a first embodiment of a nebulizer in accordance with the present invention. In accordance with the present embodiment, a nebulizer 10 is provided and it is a pneumatic nebulizer. The nebulizer 10 can turn liquid into nebulized particle. The nebulizer 10 in the present embodiment has an illustration of delivering drug for instance, but the present invention shall not be limited for this. In other embodiment, the nebulizer 10 is used to other application, for example, it adapts to the use of essential oils, cooling temperature, steamed for face and so on.

The nebulizer 10 includes a pump 20, an air pipe 30 and a nozzle 40. The pump 20 is used to inflate and generate the airflow. The air pipe 30 is connecting between the pump 20 and the nozzle 40, and used to transport the airflow generating from the pump 20 to the nozzle 40. The structure of the nozzle 40 will affect the nebulization particle size produced from the nebulizer 10 and the resistance caused by the power consumption of the pump 20. The following is more detail operation illustration of the nozzle 40.

Figure 2:
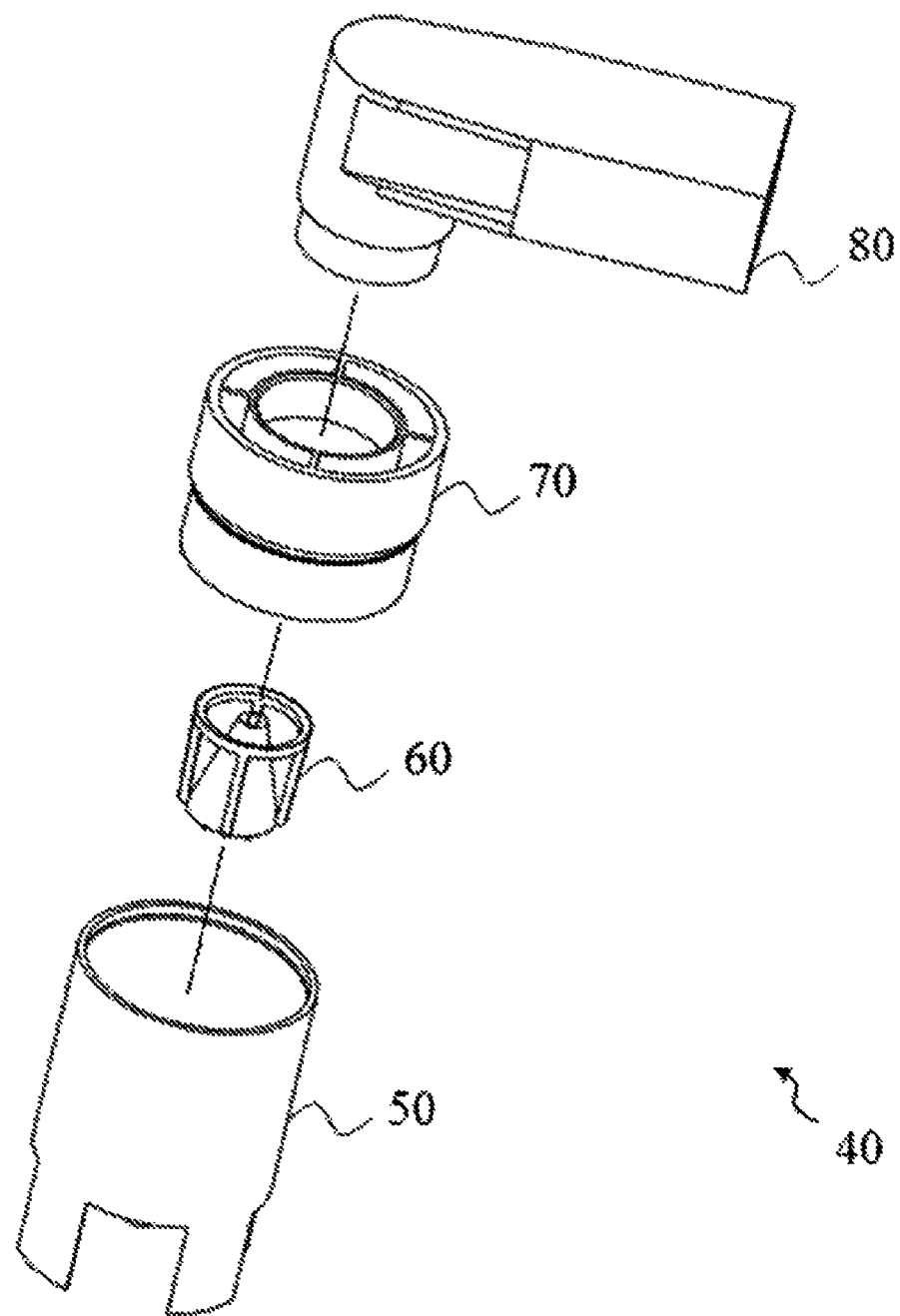
FIG. 2 is an exploded schematic perspective view of a first embodiment of a nozzle of the nebulizer in accordance with the present invention.
Figure 3:
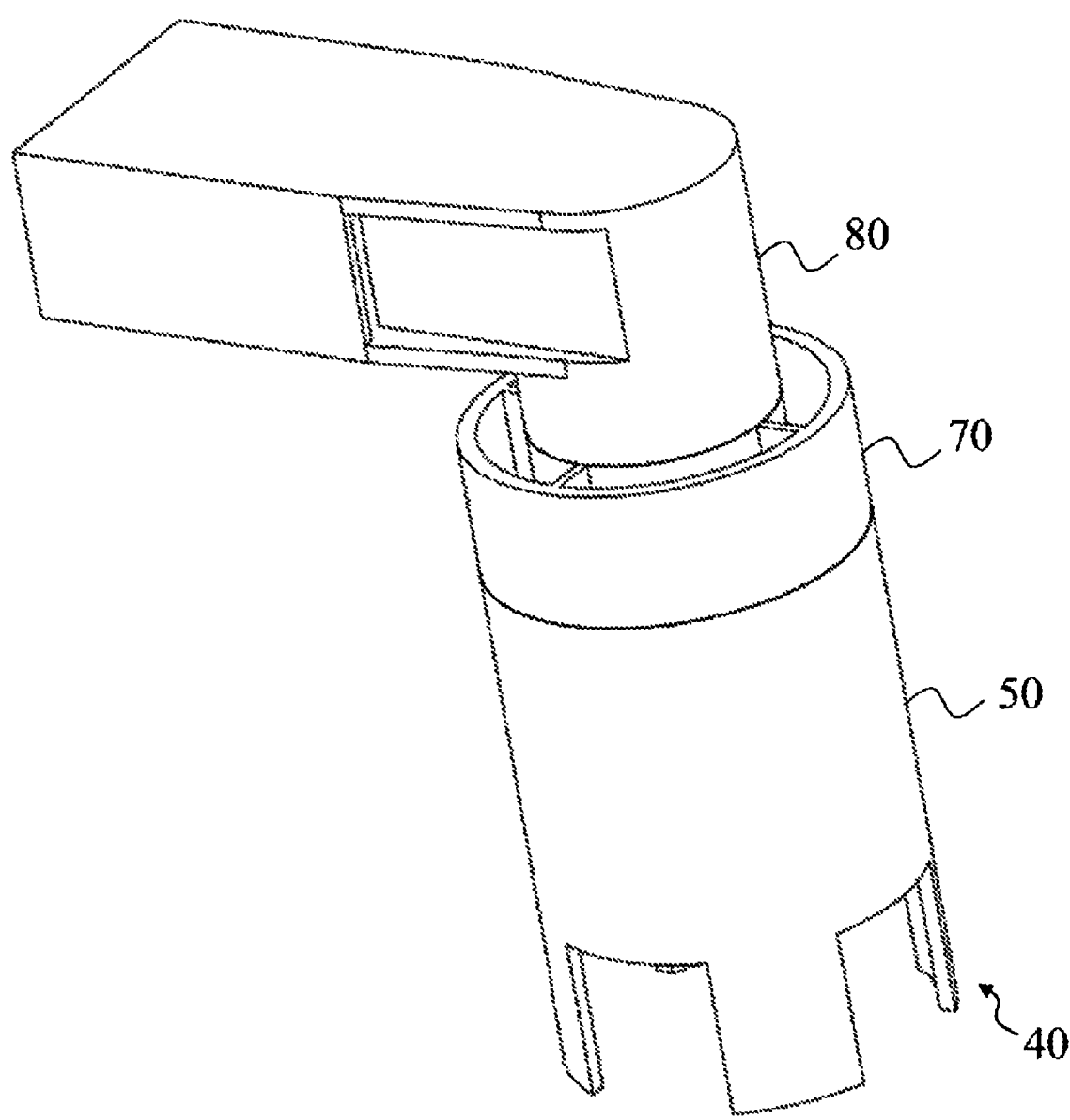
FIG. 3 is a schematic perspective view of the first embodiment of the nozzle in accordance with the present invention.
Figure 4:
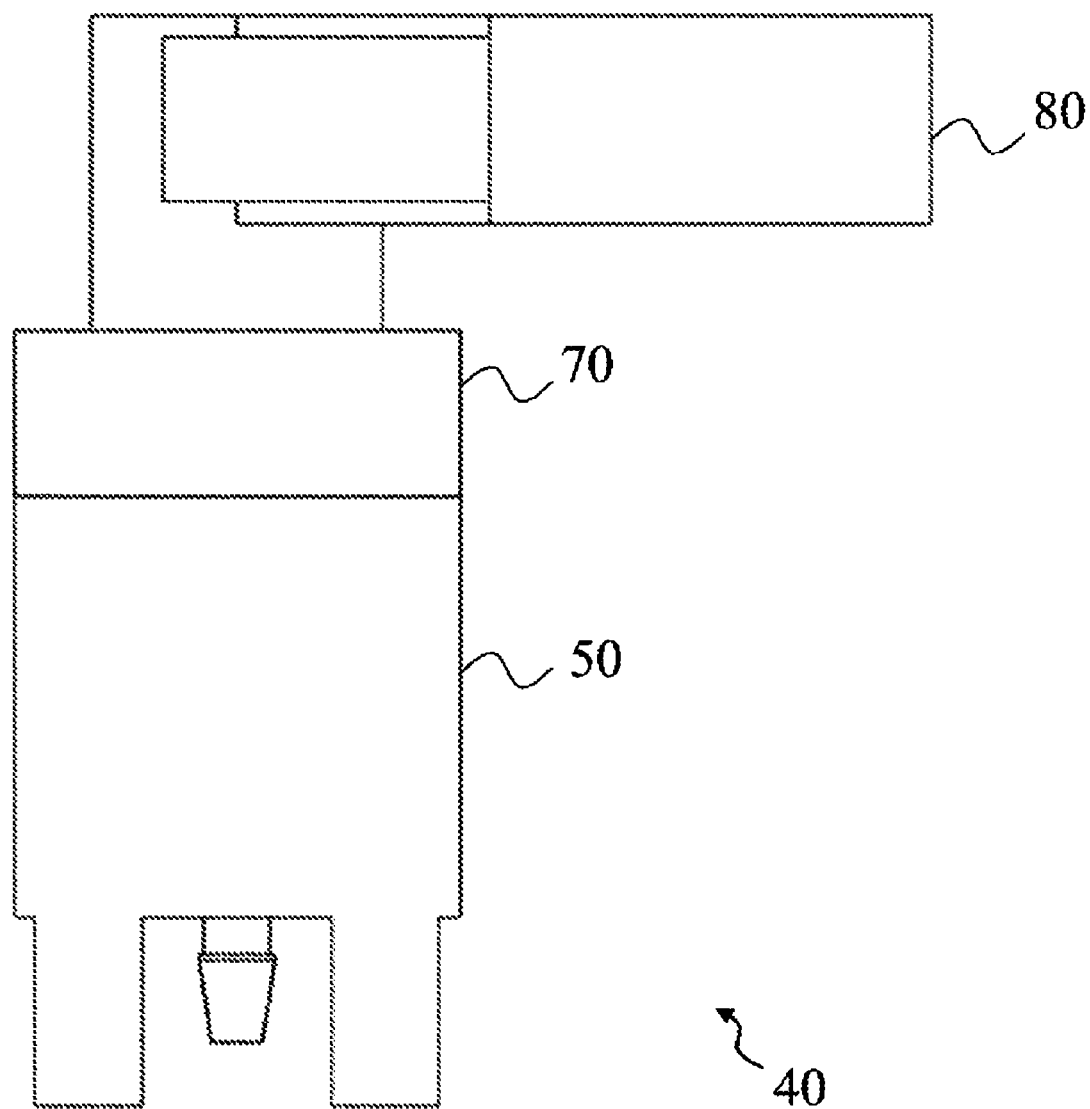
FIG. 4 is a schematic perspective view of a lateral side of the first embodiment of the nozzle in accordance with the present invention.

Please refer to FIGS. 2 to 4 in combination. FIG. 2 is an exploded schematic perspective view of a first embodiment of a nozzle of the nebulizer in accordance with the present invention. FIG. 3 is a schematic perspective view of the first embodiment of the nozzle in accordance with the present invention. FIG. 4 is a schematic perspective view of a lateral side of the first embodiment of the nozzle in accordance with the present invention. The nozzle 40 includes a containing seat 50 and a cover 70. In accordance with the present embodiment, the nozzle 40 further comprises a mouthpiece 80. The containing seat 50 is assembled with the cover 70, preferably, the containing seat 50 is screwed with the cover 70 in the present embodiment. The mouthpiece 80 has an opening at two terminals respectively. The one terminal of the mouthpiece 80 is used to assemble with the cover 70. The other one terminal size of the mouthpiece 80 is smaller than the size of user's mouth for holding so as to guide the nebulized particle passed through the user's mouth.

Figure 5:
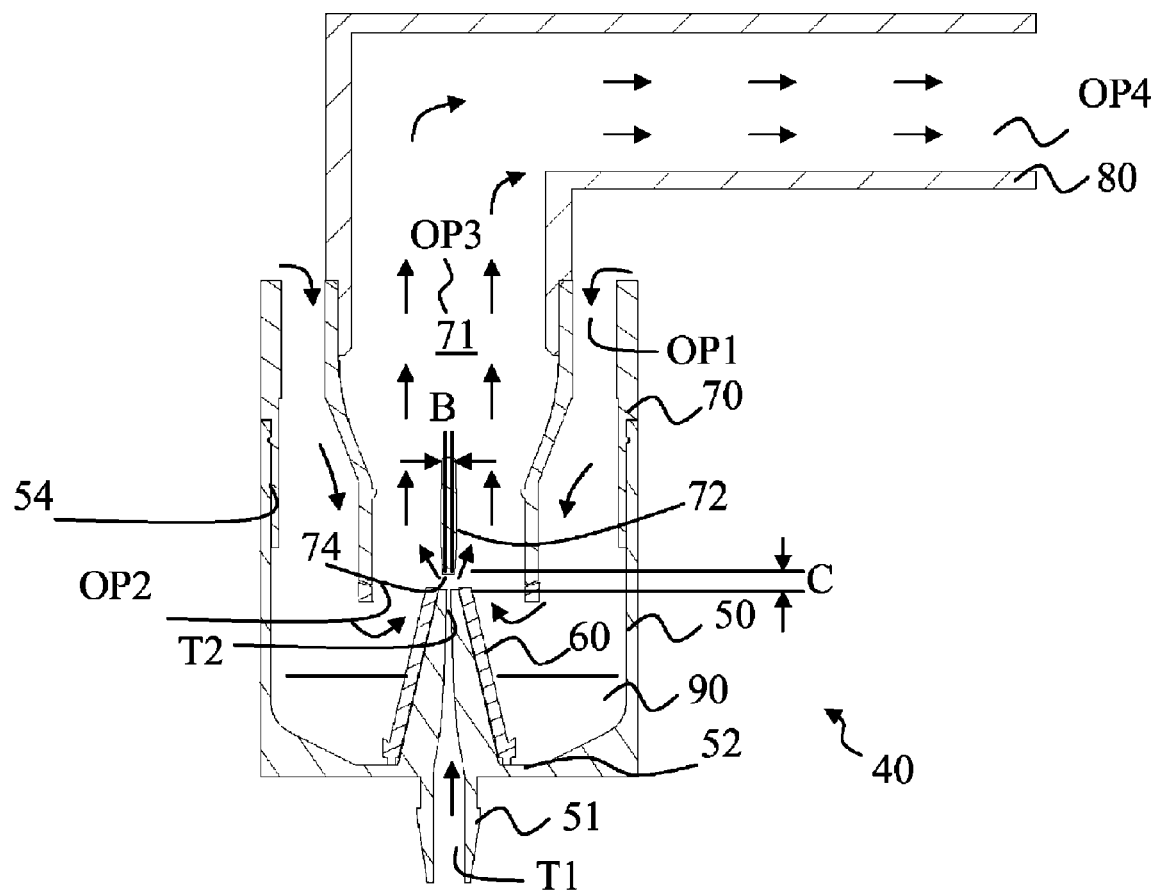
FIG. 5 is a cross-sectional view of the first embodiment of the nozzle in accordance with the present invention.

With reference to FIG. 5, it is a cross-sectional view of the first embodiment of the nozzle in accordance with the present invention. The containing seat 50 has an air conduit 51, a liquid container 52 and an opening terminal 54. In an embodiment in accordance with the present invention, the nozzle 40 further comprises a liquid delivery structure 60.

The air conduit 51 has an input terminal T1 and an output terminal T2. The input terminal T1 is used to connect with the air pipe 30 as FIG. 1 shown. The liquid delivery structure 60 is assembled in the liquid container 52, and extending from the liquid container 52 toward the output terminal T2 so as to transport liquid 90 from the liquid container 52 to the output terminal T2. More specifically, in the present embodiment, the liquid delivery structure 60 is near a wall of the liquid container 52 so as to transport the liquid 90 from the bottom of the liquid container 52 to the output terminal T2 by capillarity. In accordance with other embodiment, those skilled in the art can change the way of liquid transport as needed, but the present invention shall not be limited for this.

Figure 6:
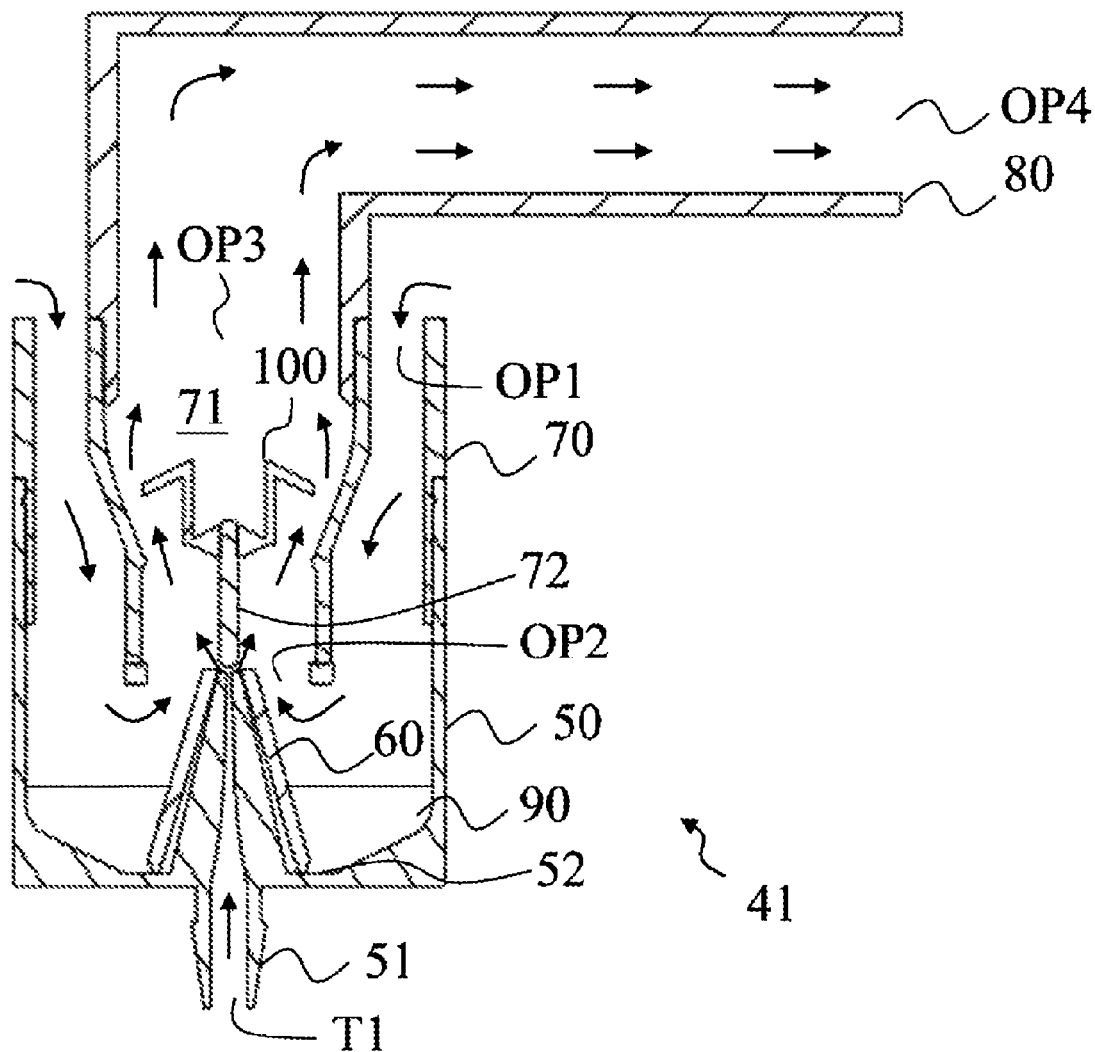
FIG. 6 is a cross-sectional view of a second embodiment of the nozzle in accordance with the present invention.

The cover 70 includes an input opening OP1, a guiding channel 71 and an impediment 72. The input opening OP1 is communicating with the opening terminal 54 of the containing seat 50. Preferably, the input opening OP1 is disposed on a periphery of the cover 70. In the present embodiment, the input opening OP1 is a circular form opening for instance. The circular form of the input opening OP1 can be one or more than one opening, but the present invention shall not be limited for this. The guiding channel 71 has a first opening OP2 and a second opening OP3 disposed oppositely to the first opening OP2. The first opening OP2 of the guiding channel 71 is communicated with the input opening OP1, and the first opening OP2 is disposed corresponding to the output terminal T2 of the containing seat 50. The impediment 72 is disposed in front of the output terminal T2 which injecting an airflow. The impediment 72 comprises a small surface 74 facing to the output terminal T2. The small surface 74 can be a flat plane (as FIG. 5 shown) or a curved surface (as FIG. 6 shown). Preferably, the small surface 74 is directly facing with the output terminal T2, and the first opening OP2 is disposed around the impediment 72 and directly facing to the output terminal T2.

To be noticed, when the pump 20 is pumping, the air will pass through the air pipe 30 and the air conduit 51 then emits from the output terminal T2. The emitted air will cause the surrounding liquid 90 lashed against the small surface 74 and subsequently flow along the first opening OP2 of the guiding channel 71 toward the second opening OP3, and subsequently flow to an opening OP4 of the mouthpiece 80, and guided the air from the input opening OP1 to the first opening OP2. The liquid 90 lashed against the impediment 72 with high speed in the air will be nebulized.

In the present embodiment, specifically, the impediment 72 is formed with the small surface 74. The liquid 90 lashed against the small surface 74 will flow to the opening OP4 in nature so as to decrease the resistance of the nebulizer 10 and keep the well nebulization efficiency.

Through continued experiment by the inventor, the width B of the small surface 74 is preferably between 0.5 mm (millimeter) to 3 mm, and the nozzle driving by the pump with the power consumption below 15 watts can produce nebulized particles with a MMAD (mass median aerodynamic diameter) of 5 microns so that the nebulization rate of liquid is between 0.15 c.c./min (cubic centimeters/minute) to 0.5 c.c./min. Preferably, the nebulization rate of liquid is between 0.15 c.c./min to 0.35 c.c./min. Furthermore, a diameter of the output terminal is 0.32 mm to 0.38 mm.

Besides, the input opening OP1 can effectively decrease the resistance of the nebulizer 10. Specifically, when the pump 20 is pumping, the air can be introduced from the input opening OP1 toward the output terminal T2 to let the airflow emitted from the output terminal T2 more smoothly flowed to the first opening OP2. In order to let the air introduced from the input opening OP1 and subsequently flow to the first opening OP2, the distance C between the impediment 72 and the output terminal T2 is preferably between 1 mm to 3 mm so that the nebulization rate of liquid is between 0.15 c.c./min to 0.5 c.c./min. Preferably, the nebulization rate of the liquid is between 0.15 c.c./min to 0.35 c.c./min for the well nebulization efficiency. Especially, if the distance C disposed between the impediment 72 and the output terminal T2 forms in the preferable range, it adapts for introducing air into the input opening OP1 which away from the output terminal T2 so as to erase the resistance caused by airflow emitted from the output terminal T2, and guides the air and liquid flowed to the first opening OP2 which closed to the output terminal T2. Preferably, the first opening OP2 is directly facing to the output terminal T2. Therefore, it lets the airflow pathway more smoothly so as to guide the air accompanied with liquid straightly flowed toward up side, and reduces the resistance of the nebulizer 10 caused by the power consumption of the pump 20. Thus, there is not only maintained the well nebulization efficiency but also avoided the resistance extremely concentrating on the output terminal T2.

In another aspect in accordance with the present invention, the present embodiment balances the resistance of the nebulizer 10 and keeps the nebulization efficiency so as to avoid the resistance extremely concentrate on part of the nozzle structure. The ways of the present invention adapts to reduce the resistance of the nebulizer 10 in order to utilize the pump 20 below 6 W of the power consumption for driving the nozzle 40 such as the impediment 72 has the small surface 74, the width of the small surface 74 is set between 0.5 mm to 3 mm, the input opening OP1 disposed away from the output terminal T2, the output terminal T2 directly facing the first opening OP2, and the distance between the impediment 72 and the output terminal T2 is set between 1 mm to 3 mm. Smaller volume of the pump 20 which power consumption below 6 watts is convenience for users to carry out and used for egression.

Although possible types of the nebulizer in accordance with the present invention has been described in the embodiment above, those skilled in the art shall recognized that the nebulizer can be designed differently. Therefore, the spirit of the present invention shall not be limited to these possible types of nebulizer in accordance with the present invention. In other words, the input opening formed on periphery of the cover and directly facing the output terminal and the impediment having a small plane or curved surface so as to reduce the resistance of the nozzle which is the key spirit and scope of the present invention. The followings are some other embodiments in accordance with the present invention for those skilled in the art to know more about the spirit of the present invention.

Generally speaking, the guiding channel of the nozzle will affect the nebulized particle size. The longer guiding channel can produce, the smaller size of nebulized particle.

Figure 7:
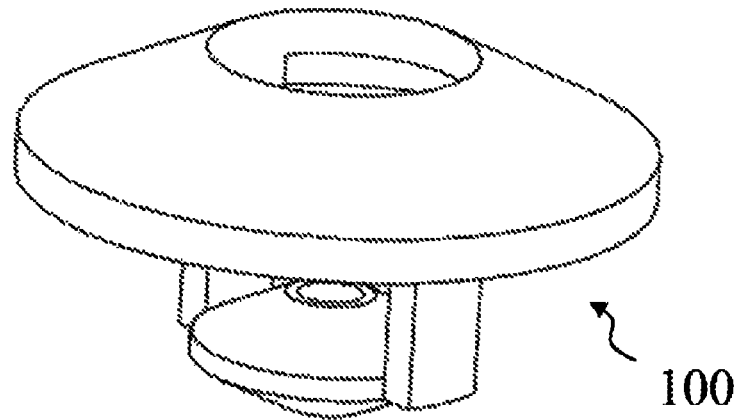
FIG. 7 is a schematic perspective view of the second embodiment of a filter in accordance with the present invention.
Figure 8:
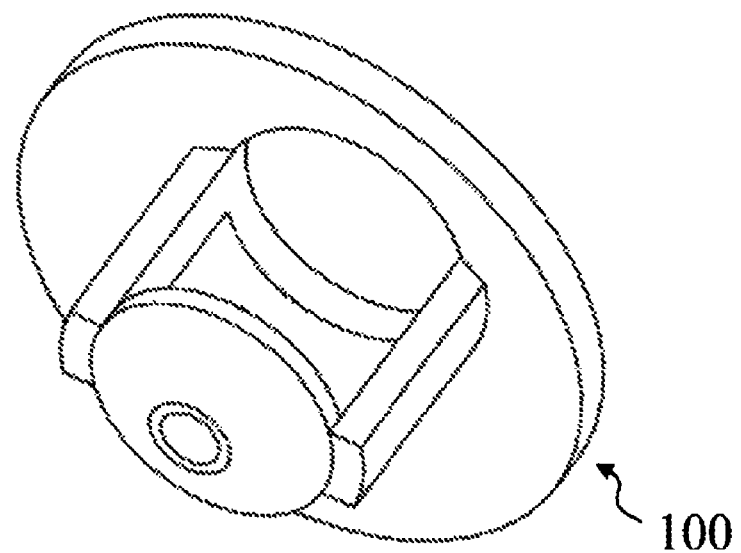
FIG. 8 is a schematic perspective view of another side of the filter in FIG. 7.

In the first embodiment, the guiding channel 71 (as shown in FIG. 5) is one choice of an embodiment of the present invention, but the present invention shall not be limited for this. In other embodiment of the present invention, those skilled in the art can change the configuration of the guiding channel 71. For example, FIG. 6 is a cross-sectional view of a second embodiment of the nozzle in accordance with the present invention. FIG. 7 is a schematic perspective view of the second embodiment of a filter in accordance with the present invention. FIG. 8 is a schematic perspective view of another side of the filter in FIG. 7. Please refer to FIGS. 6 to 8 in combination. In accordance with the second embodiment, the nozzle 41 is similar with the nozzle 40 as FIG. 5 shown. The different between the nozzle 40 and 41 is the nozzle 41 having a filter 100. In accordance with the second embodiment, the cover 70 includes the filter 100. The filter 100 is disposed in the guiding channel 71 and between the impediment 72 and the second opening OP3, and used to extend the flowing path for the air to let the smaller size of the nebulized particle passed through but the bigger size of the nebulized particle stopped for retrieving to the liquid container 52. Therefore, the nebulized particle produced by the nozzle 41 is smaller. In other embodiment of the present invention, those skilled in the art can change the type of the filter or disposed different numbers of the filter.

In accordance with the first embodiment, the nozzle 40 as FIG. 5 shown is disposed a mouthpiece 80 as an output device to let users inhaling the nebulized particle from the mouth, but it is one choice of an embodiment of the present invention and the present invention shall not be limited for this. For example, in other embodiment of the present invention, the nozzle further comprises a mask device (not shown) and the mask device also can be the output device. The mask device has a vessel and a mask. The vessel is connecting between the opening of the cover and the mask, and used to guide the airflow into the mask. Therefore, users can inhale the nebulized particle from the mask. When the nebulizer used to other application, for example, steamed face, essential oils, and so on, those skilled in the art can change the output device as needed.

Please refer to FIG. 1 and FIG. 5 in combination. Those skilled in the art can change the structure of nozzle 40 in the first embodiment as needed. For example, in accordance with the first embodiment, the air conduit 51 is one choice for instance, but in other embodiment accordance with the present invention, the air conduit 51 can dispose two or more. The air pipe 30 having bypass function can be connected with the pump 20 so as to connect with each air conduit 51.

In other example, the input opening OP1 of the nozzle 40 has an illustration of circular form for instance, but it is one choice of an embodiment of the present invention. Those skilled in the art can change the type of the input opening OP1 as needed. For example, the input opening OP1 can be disposed on the cover 70 or the containing seat 50. For example, in other embodiment of the present invention, the input opening OP1 also can be a hole or a slit formed on the wall of the containing seat 50.

In the first embodiment, the small surface 74 of the impediment 72 such as a small plane is one choice of an embodiment, the present invention shall not be limited for this. Those skilled in the art can change the type of the small surface 74, for example, the small surface 74 can be a sharp form or a smooth form of a curved surface for implement. In other example, the small surface 74 also can be a waved type or an irregular type of the plane for impediment.

In first embodiment, the width B of the small surface 74 is preferably between 0.5 mm to 3 mm. The distance C between the impediment 72 and the output terminal T2 is preferably chosen from 1 mm to 3 mm. The nebulization rate of liquid is between 0.15 c.c./min to 0.5 c.c./min. The power consumption of the pump 20 below 15 watts can drive the nozzle to produce nebulized particles with a MMAD of 5 microns. Accordingly, as description above, they are one choice of an embodiment of the present invention. Those skilled in the art can change each parameter of the nebulizer 10 as needed.

Please refer to FIG. 5, in the first embodiment, the mouthpiece 80 is detachable, but it is one choice of an embodiment of the present invention. In other embodiment, the mouthpiece 80 can integrate with the cover 70. As description above, those skilled in the art can integrate many elements together as needed. For example, the cover 70 integrates with the containing seat 50, or the liquid delivery structure 60 integrates with the containing seat 50.

Figure 9:
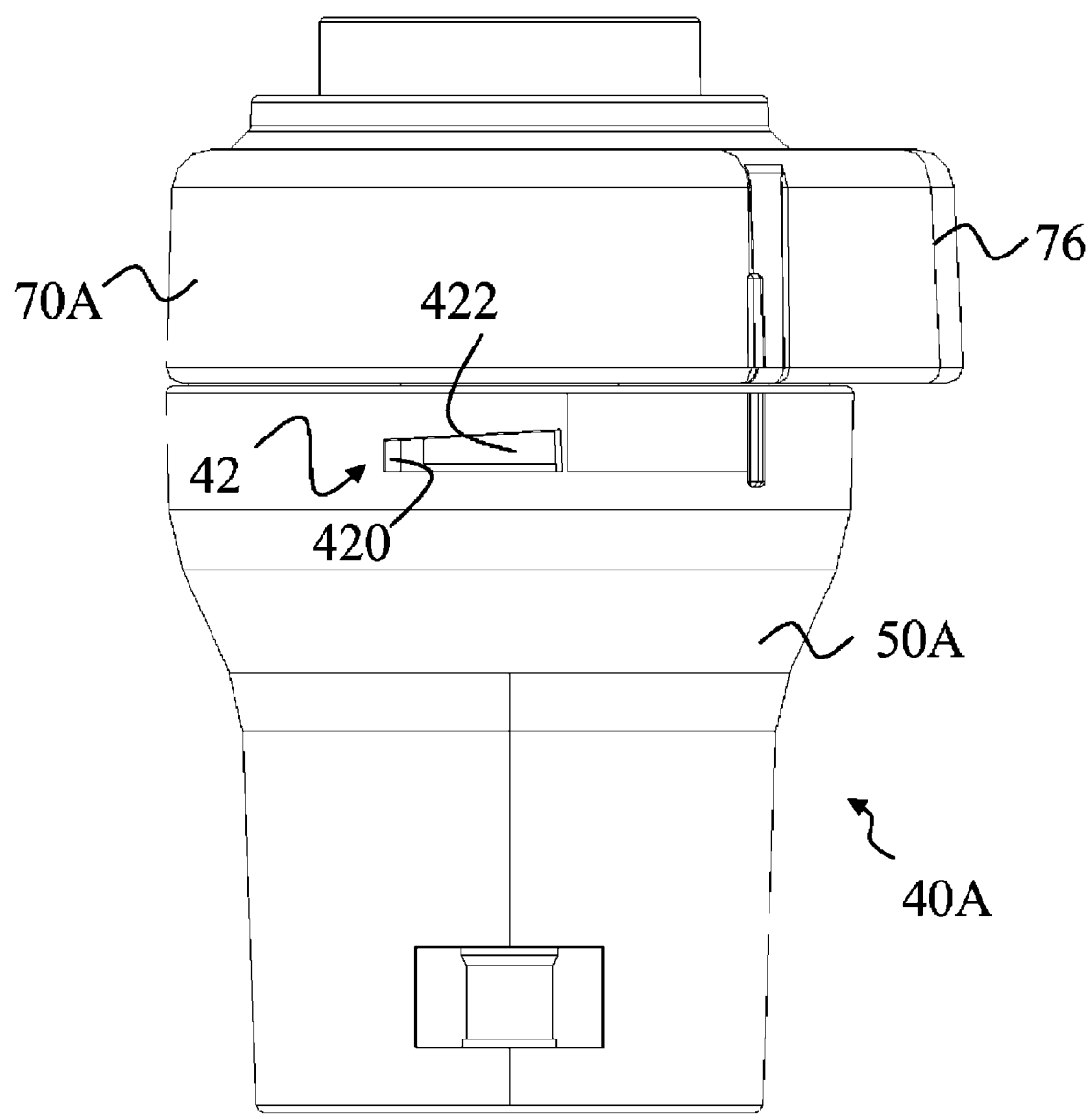
FIG. 9 is a schematic perspective view of a lateral side of a third embodiment of the nozzle in accordance with the present invention.

Please refer to FIG. 9, it is a schematic perspective view of a lateral side of a third embodiment of the nozzle in accordance with the present invention. The nozzle 40A includes a containing seat 50A and a cover 70A. The nozzle 40A different from the first embodiment is further comprising an engaging recognition element 42. The engaging recognition element 42 is used to convenient for users recognize engagement state of the containing seat 50A and the cover 70A. Preferably, the engaging recognition element 42 includes a first engagement 420 and a second engagement 422. The first engagement 420 is disposed on the containing seat 50A and the second engagement 422 is disposed on the cover 70A. Preferably, in accordance with the present embodiment, the first engagement 420 is an engaging opening on the containing seat 50A and the second engagement 422 is a protrusion on the cover 70A. Through the protrusion engaged with the engaging opening is convenient for users recognizing engagement state of the containing seat 50A and the cover 70A.

In addition, the nozzle 40A further comprises an engaging guiding element 76. The engaging guiding element 76 is used to convenient for users guide the assembly of the cover 70A and the containing seat 50A. Preferably, the engaging guiding element 76 is a block protruded from the outside of cover 70A. The block preferably is a triangle block. Users can push the triangle block so as to guide the cover 70A engagement. The engaging guiding element 76 also can form on the containing seat 50A as long as to achieve the purpose of convenient for users with guiding assembly by the engaging guiding element.

Figure 11:
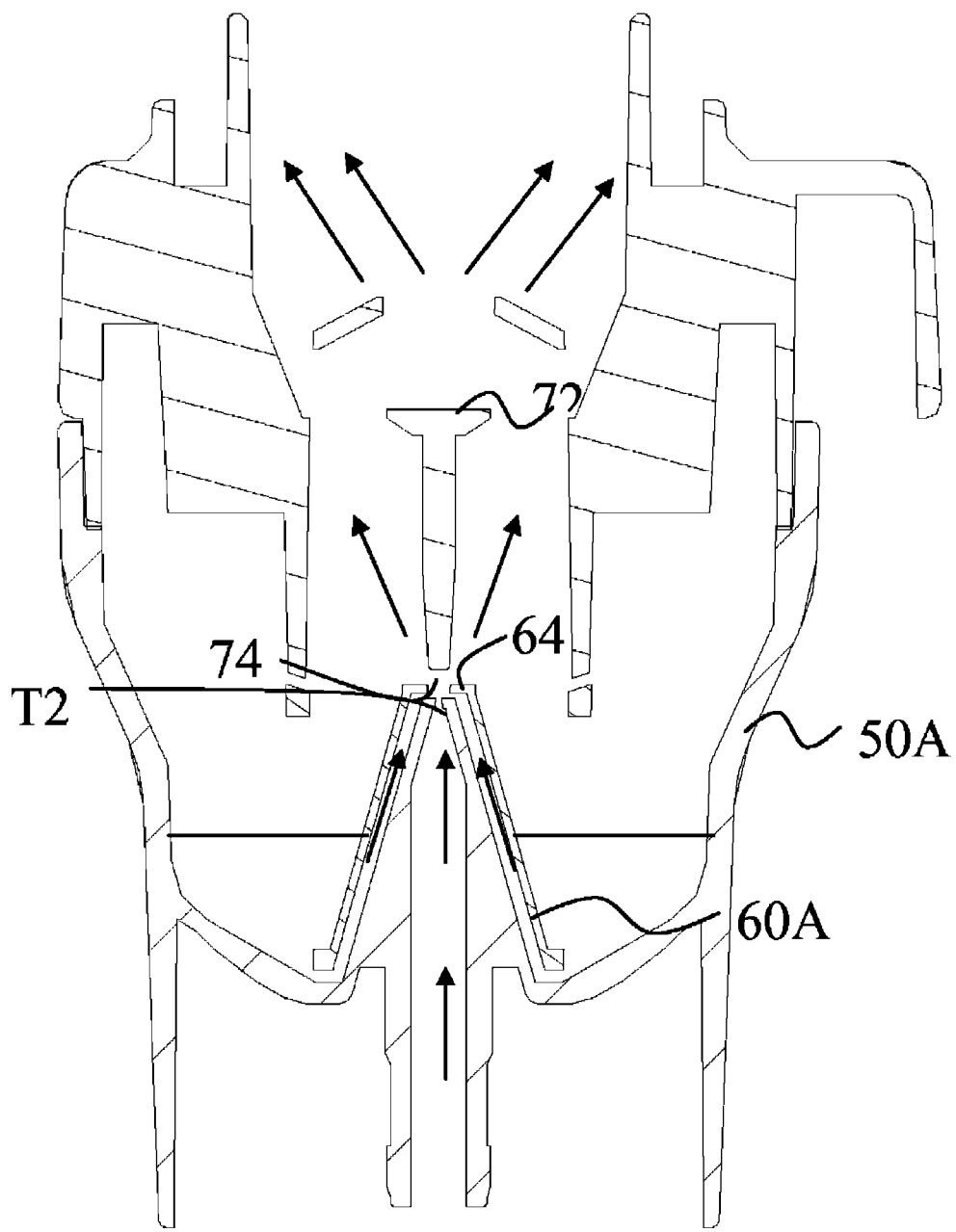
FIG. 11 is a cross-sectional view of the third embodiment of the nozzle in accordance with the present invention.

Please refer to FIGS. 10A to 10E and FIG. 11 in combination. FIGS. 10A to 10E are schematic perspective views of the other embodiment of a liquid delivery structure in accordance with the present invention. FIG. 11 is a cross-sectional view of the third embodiment of the nozzle in accordance with the present invention. The liquid delivery structure 60A is disposed in the containing seat 50A, and includes a first delivery opening 61, a second delivery opening 62 and a first liquid guiding element 64. The first delivery opening 61 and the second delivery opening 62 are disposed oppositely to each other and the first delivery opening 61 is disposed near the bottom of the containing seat 50A. Preferably, the first delivery opening 61 is bigger than the second delivery opening 62. The first liquid guiding element 64 is protruded from a plane of the second delivery opening 62. Preferably, the first liquid guiding element 64 are two semicircle protrusions protruded from the second delivery opening 62 and formed oppositely to two sites of the plane. Hence, when the liquid in the containing seat 50A along the space between the liquid delivery structure 60A and containing seat 50A delivered from the first delivery opening 61 to the second delivery opening 62, the liquid will guide along the first liquid guiding element 64 for slightly warping so as to more concentrated emit from the center. Therefore, the first liquid guiding element 64 is designed for enhancing the nebulization efficiency.

The liquid delivery structure 60A further comprises a liquid transport channel 63 and/or a second liquid guiding element 66. The liquid transport channel 63 is disposed on the plane of the liquid delivery structure 60A facing the containing seat 50A. Preferably, the liquid transport channel 63 is depressed in an inner plane of the liquid delivery structure 60A between the first delivery opening 61 and the second delivery opening 62. In the present embodiment, the liquid delivery structure 60A comprises two liquid transport channels 63 disposed opposite site in the liquid delivery structure 60A. The second liquid guiding element 66 is a block protruded on the plane of the second delivery opening 62. Preferably, the second liquid guiding element 66 is protruded on opposite side of the plane not having the first liquid guiding element 64 of the second delivery opening 62. In the present embodiment, the second liquid guiding element 66 are two square blocks. The liquid flowed along the liquid delivery structure 60A up to the first liquid guiding element 64 and/or the second liquid guiding element 66 guiding curved to let the liquid more concentrated emit from the center so as to achieve the well nebulization efficiency. In the present embodiment, a longitudinal height of the first liquid guiding element 64 is higher than that of the second liquid guiding element 66.

In the present embodiment, the liquid delivery structure 60A further comprises a plurality of convex dots protruded from an outside of the first delivery opening 61. Therefore, the liquid delivery structure 60A assembled in the containing seat 50A produces a distance relative to the containing seat 50A, and is convenient for liquid flowed along the space between the liquid delivery structure 60A and the containing seat 50A.

Accordingly, the nozzle employed in the present invention comprises the input opening in the periphery and formed the small surface, such as small plane or curved surface, on the impediment to let the guiding channel directly facing the output terminal so as to reduce the whole resistance of the nozzle. In addition, the liquid guiding element disposed on the liquid delivery structure is guiding the liquid more concentrated emitted from the center so as to achieve the well nebulization efficiency. Therefore, the nebulizer can choose the lower power consumption of the pump to drive the nozzle so that the size of nebulizer can relatively be smaller. Furthermore, there are also other advantages in some embodiments of the present invention exemplarily listed as follows:

1. The nebulizer be applied to different fields application can adapt choose the different output devices for easy to use.
2. The filter disposed on the nozzle generates smaller nebulized particle from the nebulizer.
3. The liquid delivery structure of the nozzle in accordance with the present invention can achieve predictable nebulization efficiency.

More exemplary embodiments and advantages of the present invention may be ascertained by reviewing the present disclosure and the accompanying drawing. It is intended that the description and embodiments with reference to the accompanying drawing to be considered as exemplary only.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Other embodiments of the invention will appear to those skilled in the art from consideration of the specification and practice of the invention disclosed herein. It is intended that the specification and examples to be considered as exemplary only, with a true scope and spirit of the invention being indicated by the following claims.

What is claimed is:

1. A nozzle for a nebulizer used for respiratory treatment, comprising:
   a containing seat comprising:
      an air conduit having an input terminal and an output terminal; and
      a liquid container used for storing liquid;
   a liquid delivery structure assembled in the liquid container and comprising:
      a first delivery opening;
      a second delivery opening disposed oppositely to the first delivery opening to let the liquid transport from the first delivery opening to the second delivery opening;
      a first liquid guiding block; and
      a second liquid guiding block and the first liquid guiding block both protruding from the second delivery opening, wherein a longitudinal height of the first liquid guiding block is higher than that of the second liquid guiding block; and
   a cover comprising:
      a guiding channel having a first opening and a second opening disposed oppositely to each other; and an impediment disposed in front of and facing the output terminal, wherein the first liquid guiding block and/or the second liquid guiding block guide the liquid extending toward a center of the output terminal so that the liquid more concentrates to the impediment;

wherein air is configured to be emitted from the output terminal and accompanies with the liquid to lash against the impediment and subsequently flow to the second opening of the guiding channel.

2. The nozzle as claimed in claim 1, further comprising an input opening used for introducing air.

3. The nozzle as claimed in claim 2, wherein the cover is assembled with the containing seat and has a circumference space and an inner space, the first and the second opening both disposed at the inner space, and the input opening disposed at an upside of the circumference space of the cover so as to let an introduced air entering direction parallel with an air flow direction of the inner space.

4. The nozzle as claimed in claim 3, wherein the first opening is communicated with the input opening, and the first opening is near the output terminal and the input opening is away from the output terminal.

5. The nozzle as claimed in claim 1, wherein the impediment comprises a small surface facing the output terminal and the air emitted from the output terminal is configured to lashed the small surface.

6. The nozzle as claimed in claim 5, wherein the small surface is a small flat plane or a curved surface.

7. The nozzle as claimed in claim 6, wherein the width of the small plane is between 0.5 millimeter to 3 millimeter.

8. The nozzle as claimed in claim 6, wherein the nozzle is adapted to be driven by a pump and a power consumption of the pump is below 15 watts to produce nebulized particles to reach a mass median aerodynamic diameter of 5 microns, and a diameter of the output terminal is 0.32 millimeter to 0.38 millimeter.

9. The nozzle as claimed in claim 8, wherein the nozzle is adapted to the nebulizer which has a nebulization rate of liquid between 0.15 cubic centimeters/minute to 0.5 cubic centimeters/minute.

10. The nozzle as claimed in claim 1, wherein an input opening is formed in the containing seat or the cover.

11. The nozzle as claimed in claim 10, wherein the first opening is disposed in front of and directly facing the output terminal.

12. The nozzle as claimed in claim 1, wherein the cover further comprises a filter disposed in the guiding channel between the impediment and the second opening, and the filter is used to extend a flowing path of the air.

13. The nozzle as claimed in claim 1, further comprising an engaging guiding block being used to guide the cover and the containing seat during assembly.

14. The nozzle as claimed in claim 13, wherein the engaging guiding block is on an outside of the cover.

15. The nozzle as claimed in claim 1, further comprising a recognition engaging element disposed on the cover and the containing seat, and used to recognize an engagement state of the cover and the containing seat.

16. The nozzle as claimed in claim 15, wherein the recognition engaging element is visible from the outside of the nozzle.

17. A nebulizer used for respiratory treatment, comprising a containing seat comprising:

an air conduit having an input terminal and an output terminal; and a liquid container used for storing liquid;

a pump used to pump air into the input terminal;

an air pipe connecting between the pump and the input terminal;

a liquid delivery structure assembled in the liquid container and comprising:

a first delivery opening;

a second delivery opening disposed oppositely to the first delivery opening to let the liquid transport from the first delivery opening to the second delivery opening;

a first liquid guiding block; and a second liquid guiding block and the first liquid guiding element both protruding from the second delivery opening, wherein a longitudinal height of the first liquid guiding block is higher than that of the second liquid guiding block; and a cover comprising:

a guiding channel having a first opening and a second opening disposed oppositely to each other; and an impediment disposed in front of and facing the output terminal, wherein the first liquid guiding block and/or the second liquid guiding block guide the liquid extending toward a center of the output terminal so that the liquid more concentrates to the impediment;

wherein air is configured to be emitted from the output terminal and accompanies with the liquid to lash against the impediment and subsequently flow to the second opening of the guiding channel.

18. The nebulizer as claimed in claim 17, wherein the impediment comprises a small surface facing the output terminal and air emitted from the output terminal is configured to lashed the small surface.

19. The nebulizer as claimed in claim 17, wherein the width of the small plane is between 0.5 millimeter to 3 millimeter.

20. A nozzle for a nebulizer, comprising a containing seat comprising:

an air conduit having an input terminal and an output terminal; and a liquid container used for storing liquid;

a liquid delivery structure assembled in the liquid container and comprising:

a first delivery opening;

a second delivery opening disposed oppositely to the first delivery opening to let the liquid transport from the first delivery opening to the second delivery opening;

a first liquid guiding block; and a second liquid guiding block and the first liquid guiding element both protruding from the second delivery opening, wherein a longitudinal height of the first liquid guiding block is higher than that of the second liquid guiding block; and a cover comprising:

a guiding channel having a first opening and a second opening disposed oppositely to each other; and an impediment disposed in front of and facing the output terminal, wherein the first liquid guiding block and/or the second liquid guiding block guide the liquid extending toward a center of the output terminal so that the liquid more concentrates to the impediment;

wherein a distance between the impediment and the output terminal is between 1 millimeter to 3 millimeter and air is configured to be emitted from the output terminal and accompanies with the liquid to lash against the impediment and subsequently flow to the second opening of the guiding channel.

\* \* \* \* \*